United States Patent [19]

Keil et al.

[11] Patent Number: 6,162,945
[45] Date of Patent: Dec. 19, 2000

[54] PROCESS FOR PREPARING 2-(2-METHYLPHENYL)-3-METHOXYACRYLIC ACID METHYLESTER

[75] Inventors: Michael Keil, Freinsheim; Josef Wahl, Schifferstadt, both of Germany

[73] Assignee: BASF Aktiengesellschaft, Ludwigshafen, Germany

[21] Appl. No.: 09/117,656

[22] PCT Filed: Feb. 17, 1997

[86] PCT No.: PCT/EP97/00728

§ 371 Date: Aug. 4, 1998

§ 102(e) Date: Aug. 4, 1998

[87] PCT Pub. No.: WO97/30020

PCT Pub. Date: Aug. 21, 1997

[30] Foreign Application Priority Data

Feb. 17, 1996 [DE] Germany .................. 196 05 901

[51] Int. Cl.⁷ .................................................. C07C 69/612
[52] U.S. Cl. ........................................................... 560/60
[58] Field of Search ............................................ 560/60

[56] References Cited

U.S. PATENT DOCUMENTS 5,438,059 8/1995 Clough et al. ...................... 514/256

FOREIGN PATENT DOCUMENTS 378 308 A1 7/1990 European Pat. Off. .
94/05622 3/1994 WIPO .

*Primary Examiner*—Cecilia Tsang
*Assistant Examiner*—Sonya N Wright

*Attorney, Agent, or Firm*—Keil & Weinkauf

[57] ABSTRACT

A process for preparing methyl 2-(2-methylphenyl)-3-methoxyacrylate (I)

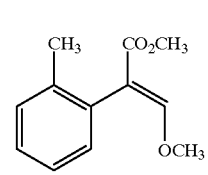

by formylation of methyl 2-methylphenylacetate (II)

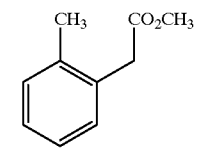

in an inert solvent in the presence of a base, and subsequent methylation of the enolate III formed

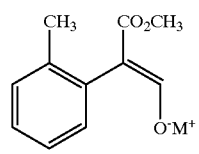

where $M^+$ is an alkali metal cation.

13 Claims, No Drawings

PROCESS FOR PREPARING 2-(2-METHYLPHENYL)-3-METHOXYACRYLIC ACID METHYLESTER

This application is a 371 of PCT/EP97/00728 filed Feb. 17, 1997.

The present invention relates to a process for preparing methyl 2-(2-methylphenyl)-3-methoxyacrylate (I)

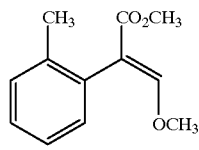
(I)

by formylation of methyl 2-methylphenylacetate (II)

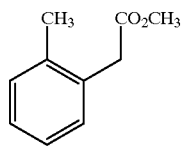
(II)

in an inert solvent in the presence of a base, and subsequent methylation of the enolate III formed

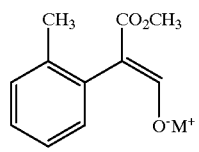
(III)

where $M^+$ is an alkali metal cation.

The preparation of methyl 2-(2-methylphenyl)-3-methoxyacrylate is described in many places in the literature (cf. EP-A 178 826, EP-A 203 606, EP-A 226 917, EP-A 473 980 and WO-A 94/05,622).

EP-A 178 826 describes the use of dimethylformamide as inert solvent and sodium hydride as base for the formulation. The formylation takes place at 0–5° C. The subsequent methylation is carried out in dimethylformamide using dimethyl sulfate in the presence of potassium carbonate. Similar reactions are disclosed in EP-A 243 012, EP-A 273 572, EP-A 329 011 and EP-A 480 795.

EP-A 203 606 and EP-A 226 917 disclose formylation in ether in the presence of sodium hydride at the boiling point of the mixture. The subsequent methylation is carried out in acetone using dimethyl sulfate in the presence of potassium carbonate.

In another variant, 3-alkoxy-2-heteroazolylaminoacrylic esters are obtained by formylation in dimethylformamide in the presence of alkali metal alcoholates at 0–5° C. and subsequent methylation using dimethyl sulfate (EP-A 473 980).

In addition, WO-A 94/05,622 describes the preparation of methyl 2-(2-methylphenyl)-3-methoxyacrylate (I) by formylation in hydrocarbons in the presence of a phase-transfer catalyst.

These known processes have the disadvantage that
the procedure and workup are in some cases very complicated so that reaction on the industrial scale is possible only with provisos,
the resulting yields are unsatisfactory and
the product is formed as mixture of isomers (E+Z).

With a view to the use of methyl 2-(2-methylphenyl)-3-methoxyacrylate (I) as starting material for the active substances disclosed in the literature cited at the outset, it is desirable to have a process which can be used industrially and which, additionally, results substantially in the E isomer with good overall yields.

A process has accordingly been found for preparing methyl 2-(2-methylphenyl)-3-methoxyacrylate (I) by formylation of methyl 2-methylphenylacetate (II) in an inert solvent in the presence of a base, and subsequent methylation of the enolate III formed, where $M^+$ is an alkali metal cation, wherein an organic aprotic dipolar solvent is used as inert solvent and an alkali metal alcoholate is used as base.

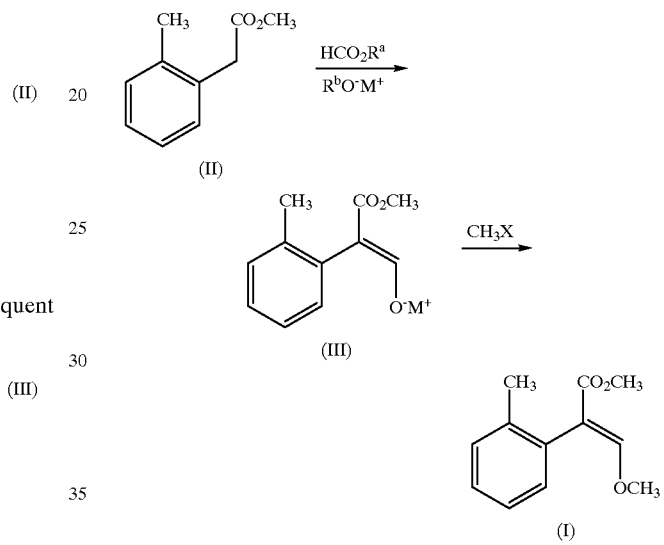

$R^a$ (ester of formic acid) and $R^b$ (alcoholate residue) are, independently of one another, alkyl groups, especially $C_1$–$C_4$-alkyl such as methyl, ethyl, propyl, isopropyl, butyl, sec-butyl, isobutyl and tert-butyl, in particular methyl.

X in the methylating reagent is a halogen atom (in particular chlorine, bromine and iodine) or an equivalent of a sulfate group.

The procedure for the process according to the invention is generally such that methyl 2-methylphenylacetate (II) and the alkyl formate are introduced into the inert aprotic polar solvent, and a solution of the alcoholate in the corresponding alcohol is added to this mixture at from –10° C. to 50° C., preferably 10° C. to 30° C., in particular 15° C. to 25° C.

The inert solvent used in the process according to the invention is generally an organic aprotic polar solvent, the nature of the solvent used normally having no effect on the course of the reaction. With a view to the workup of the reaction mixture, it has proven advantageous to use dimethylformamide, N-methylpyrrolidone, dimethyl sulfoxide, N,N-dimethylacetamide or N-methylformanilide, especially N-methylpyrrolidone, because these solvents can easily be removed from the product by distillation.

The amount of solvent used is likewise of only minor importance for success of the process. The amount should in any event be sufficient to ensure uniform distribution of the reactants. Larger amounts of solvent are not in general an impediment but are undesirable from the economic viewpoint. About 1000 ml to 3000 ml of solvent are normally used per mole of (II), preferably 1000 ml to 1500 ml.

In the reaction according to the invention, the alkyl formate is used in at least molar amounts (1 mol per mole of II). Since the alkyl formate may additionally act as solvent or diluent, it is preferably used in an excess of up to 20 mol per mole of II. Larger amounts of alkyl formate are not an impediment but are undesirable from the economic viewpoint.

The alkali metal alcoholate normally used is a sodium or potassium salt of lower alcohols, eg. with 1 to 4 carbon atoms, in particular potassium or sodium methoxide, potassium or sodium ethoxide, and potassium or sodium tert-butoxide. Sodium methoxide and potassium tert-butoxide are particularly preferred from the economic viewpoint. Sodium methanolate is used in particular.

The alkali metal alcoholate is used in at least molar amounts (1 mol of alcoholate per mole of II) in the reaction according to the invention. In order to avoid losses of yield, it has proven advantageous to use the alcoholate in an excess of about 0.5 mol to 3 mol, preferably 1.5 mol to 2.5 mol. The amount of alcoholate should not be chosen to be too high because, otherwise, the methylation in the subsequent reaction may be impeded.

The alcoholate can in general be used undiluted or as suspension or solution in the corresponding alcohol.

The enolate III formed in the process according to the invention is not isolated. The reaction mixture obtained on reaction of II with the alkyl formate is merely freed of more volatile constituents under reduced pressure and at elevated temperature. The temperature in this case should not exceed 130° C. because decomposition (CO elimination) of the product is observed above this temperature. The minimum temperature depends on the nature of the alcoholate used and on the pressure. In general, the distillation is carried out under from 1000 to 20 mbar, preferably 20 to 2 mbar.

Results to date indicate that protic components (eg. water of reaction or alcohols) may interfere with further conversion of the enolate into the product (I). The distillation of the more volatile constituents should therefore ensure removal of these constituents as far as possible.

The reaction mixture which has been concentrated to about ⅔ to ½ of its original volume can be used without further purification for the methylation in the process according to the invention. The procedure for this is normally to dilute the reaction mixture with an organic aprotic polar solvent, preferably the solvent used in the first reaction step, and subsequently to add the methylating reagent to the diluted mixture.

The solvents mentioned at the outset are used as organic aprotic polar solvent, the nature of the solvent used normally having no effect on the course of the reaction. With a view to the workup of the reaction mixture, it has likewise proven advantageous to use dimethylformamide, N-methylpyrrolidone, dimethyl sulfoxide, N,N-dimethylacetamide or N-methylformanilide, especially N-methylpyrrolidone, since these solvents can easily be removed from the product by distillation.

The amount of solvent used is likewise of only minor importance for success of the process. The amount should in any event be sufficient to ensure uniform distribution of the reactants. Larger amounts of solvent are not in general an impediment but are undesirable from the economic viewpoint. About 1000 ml to 3000 ml of solvent are normally used per mole of (II), preferably 1000 ml to 1500 ml.

Suitable methylating agents are the conventional methylating reagents, eg. methyl halides such as methyl chloride, bromide and iodide, and dimethylformamide.

The methylating agent is used in at least molar amounts (1 mol per mole of II) in the process according to the invention. Since the methylating agent reacts with residues of the alkali metal alcoholate which are still present, it is advisable to use an excess. The excess depends essentially on the excess in which the alcoholate was used in the first reaction stage. Excess amounts of methylating agent have no relevance to the reaction and should be avoided merely on economic considerations.

The temperature during the methylation should generally be below 50° C., because there is noticeable decomposition of the enolate II or of the acrylic ester (I) above this temperature. Otherwise, the reaction temperature normally depends essentially on the nature of the methylating reagent used. When volatile methylating agents such as methyl halides are used, the temperature should be chosen appropriately low, whereas a higher temperature can be chosen when involatile methylating agents such as dimethyl sulfate are used.

On methylation with methyl chloride, a temperature of from 0° C. to 50° C., preferably 0° C. to 30° C., has proven advantageous for the reaction.

The resulting reaction mixture is worked up in a conventional way by first substantially removing the volatile constituents under reduced pressure and purifying the resulting residue by extraction. The product can be further purified by fractional distillation where appropriate.

Experience has shown that the solvents and reagents recovered during removal of the volatile constituents can be reused in the reaction.

Example of the process:

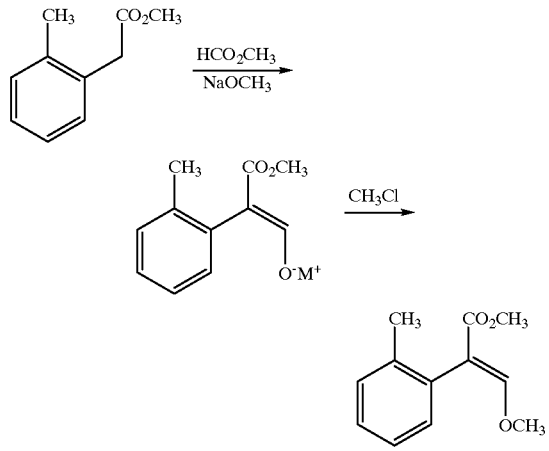

720 g of methyl formate were added to a mixture of 2000 ml of N-methylpyrrolidone and 328 g (2 mol) of methyl 2-methylphenylacetate at 20–25° C. After about 15 min, 540 g of sodium methoxide solution (30% strength in methanol) were added to the mixture. After the addition was complete, the pressure was reduced stepwise to 20–2 mbar, and the mixture was slowly heated to 80° C., during which a mixture of methanol, methyl formate and N-methylpyrrolidone distilled out (about 1400 ml in total).

The resulting residue was taken up in 450 ml of N-methylpyrrolidone, and 180 g (3.6 mol) of methyl chloride (gaseous) were passed into the mixture at 10–20° C. After about 12 h, the excess methyl chloride and the resulting dimethyl ether were removed at 50° C. under 20 mbar, and subsequently about 1640 g of N-methylpyrrolidone were removed at 80° C. under 2 mbar.

The resulting residue was taken up in 5000 ml of water and extracted 3 times with 2000 ml of toluene each time. The organic phase was washed once with 2000 ml of water, dried and concentrated under reduced pressure (water pump vacuum).

Fractional distillation through a 50 cm packed column resulted in 358 g of the enol ether (boiling point (0.5): 104–115° C., GC purity: 99.3%=89% of theory; E:Z isomers=98:2).

We claim:

1. A process for preparing methyl 2-(methylphenyl)-3-methoxyacrylate

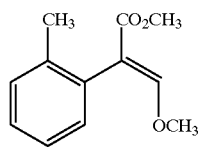

(I)

which comprises: reacting an alkyl formate with methyl 2-methylphenylacetate (II)

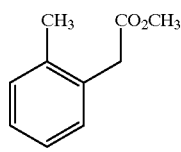

(II)

in an inert solvent in the presence of a base, to form an enolate III

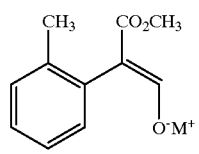

(III)

where M$^+$ is an alkali metal cation and subsequently reacting the enolate III with a methylating agent without isolating the enolate, wherein an organic aprotic dipolar solvent is used as inert solvent, and an alkali metal alcoholate is used as base.

2. The process of claim 1, wherein dimethylformamide, N-methylpyrrolidone, dimethyl sulfoxide, N,N-dimethylacetamide or N-methylformanilide is used as inert solvent.

3. The process of claim 1, wherein an alkali metal methanolate is used as alkali metal alcoholate.

4. The process of claim 1, wherein a sodium or potassium alcoholate is used as alkali metal alcoholate.

5. The process of claim 1, wherein a $C_1$–$C_4$-alkyl formate is used as formylating agent.

6. A process of claim 5, wherein methyl formate is used as formylating agent.

7. The process of claim 1, wherein a methyl halide or dimethyl sulfate is used as methylating agent.

8. The process of claim 7, wherein methyl chloride, bromide or iodide is used as methylating agent.

9. The process of claim 1, wherein the formylation is carried out at from −10 to 50° C.

10. The process of claim 9, wherein the formylation is carried out at from 10 to 30° C.

11. The process of claim 1, wherein the methylation is carried out at from −10 to 50° C.

12. The process of claim 11, wherein the methylation is carried out at from 10 to 30° C.

13. A process for preparing methyl 2-(methylphenyl)-3-methoxyacrylate (I)

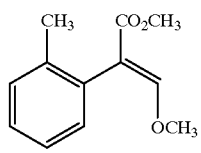

(I)

which comprises: reacting an alkyl formate with methyl 2-methylphenylacetate (II)

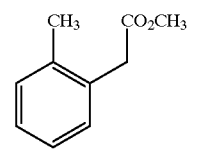

(II)

in an inert solvent in the presence of a base, to form an enolate III

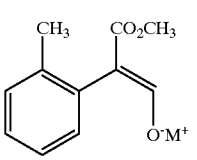

(III)

where M$^+$ is an alkali metal cation and subsequently reacting the enolate III with a methylating agent without isolating the enolate, wherein N-methylpyrrolidone is used as inert solvent, and an alkali metal alcoholate is used as base.

* * * * *